United States Patent [19]

Gross et al.

[11] 4,000,203
[45] Dec. 28, 1976

[54] PRODUCTION OF ORTHOPHENYLPHENOLS
[75] Inventors: David E. Gross, St. Charles; Norman A. Fishel, Olivette, both of Mo.
[73] Assignee: Monsanto Company, St. Louis, Mo.
[22] Filed: Aug. 8, 1975
[21] Appl. No.: 603,066
[52] U.S. Cl. ............................ 260/620; 260/520 D; 260/520 E; 260/619 R; 260/619 D; 260/600 R
[51] Int. Cl.² ................ C07C 37/00; C07C 45/00; C07C 51/00
[58] Field of Search ........... 260/620, 619 R, 619 D, 260/600 R, 520 E, 520 D

[56] References Cited
UNITED STATES PATENTS

| | | | |
|---|---|---|---|
| 2,244,244 | 6/1941 | Deseke | 260/620 |
| 2,682,035 | 11/1958 | Muller et al. | 260/620 |
| 3,169,149 | 2/1965 | Walsh | 260/620 |
| 3,549,712 | 12/1970 | Hay et al. | 260/620 |
| 3,567,787 | 3/1971 | Hennis | 260/620 |
| 3,655,522 | 4/1972 | Seeburger et al. | 260/620 |

OTHER PUBLICATIONS

Landa et al., "Sb. Vysokeskoly Chem–Technol Praze, Technol Paliv", 16, 159–170 (1969).
Shuikin et al., "J. Gen. Chem. USSR", 29, 2932 (1959).

*Primary Examiner*—Norman Morgenstern
*Attorney, Agent, or Firm*—Joseph D. Kennedy

[57] ABSTRACT

The present invention relates to a process for the preparation of orthophenylphenol and derivatives thereof, specifically by the reaction of dibenzofuran and its derivatives with hydrogen, at elevated temperatures, in the presence of a catalyst comprised of one or more Group VIII elements dispersed on a porous magnesia support.

9 Claims, No Drawings

PRODUCTION OF ORTHOPHENYLPHENOLS

BACKGROUND OF THE INVENTION

This invention relates to a process for the preparation of orthophenylphenol and its derivatives. More particularly, it relates to a process for the reaction of dibenzofuran and its derivatives with hydrogen, at elevated temperatures, in the presence of a catalyst comprised of one or more Group VIII elements on a porous magnesia support.

Dibenzofuran may be represented by the following formula numbered according to Chemical Abstracts (1973)

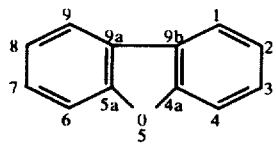

Under the influence of a catalyst a hydrogenolysis reaction takes place, whereby one of the two carbon-oxygen bonds of the furan structure in dibenzofuran may be cleaved with the subsequent addition of hydrogen to each of these sites, for example, the bond between the numbered members (5) and (5a) or (5) and (4a) may be cleaved with subsequent addition of hydrogen to form orthophenylphenol product.

It will, therefore, be understood that derivatives of dibenzofuran used in this process of the present invention for preparing derivatives of orthophenylphenol should include a heterocyclic ring of at least five members with oxygen being the hetero atom, and the ring thereof containing unsaturation at each of the carbon atoms attached to said hetero oxygen atom. It should also be understood that the carbocyclic rings in dibenzofuran and its derivatives may be partially saturated so long as the heterocyclic ring oxide contains unsaturation at each of the carbon atoms attached to said hetero oxygen atom.

The derivatives of dibenzofuran for the process of this invention may be represented by the formula

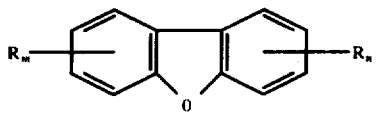

where $n$ is an integer from 0 to 2, $m$ is an integer from 1 to 2, and each R may be selected from cycloalkyl of 5 to 7 carbon atoms, alkylated cycloalkyl of 6 to 11 carbon atoms, phenyl, benzylphenyl, diphenylyl, alkylated phenyl of 7 to 19 carton atoms, naphthyl and alkylated naphthyl of 11 to 14 carbon atoms.

The following substituents are illustrative of those which may be represented by R; cyclopentyl, cicyclohexyl, cycloheptyl, 2-ethylcyclohexyl, 2-ethylcyclopentyl, 3-propylcycloheptyl, tolyl, ethylphenyl, isopropylphenyl, n-hexylphenol, 3-methyl-hexylphenyl, cumyl, 2,6-diisopropylphenol, 1-naphthyl, 2-naphthyl, methylnaphthyl, ethylnaphthyl, t-butylnaphthyl, dimethylnaphthyl or the like.

It should be noted that, in addition to the R substituents, the carbocyclic rings may contain a lower alkyl substituent straight chain or branched such as methyl, ethyl, propyl, isopropyl, butyl or an oxygen containing substituent such as hydroxyl, carbonol, aldehyde, carboxylic acid and the like.

R may also represent the addition of a 4 carbon chain in such a manner as to effect the formation of a benzenoid type fused ring structure giving rise to such compounds as dinaphthofurans, benzonaphthofurans and substituted derivatives thereof.

It will also, therefore, be understood that Group VIII elements used in the process of the present invention for preparing orthophenylphenol and its derivatives shall include one or more of the following named elements: platinum, palladium, iridium, osmium, rhodium, ruthenium, nickel, iron and cobalt.

Orthophenylphenol and its derivatives are useful for the preparation of dyestuffs, for example 2,2'-dihydroxydiphenyl which is described in U.S. Pat. No. 3,169,149. Orthophenylphenol is also useful as an antimicrobial agent, for example, as a fungicide for the postharvest treatment of citrus fruit [McCornack, Proc. Fla. State Hort. Soc., 83, 229–32 (1970)], as a biocidal agent or preservative for wood chips (U.S. Pat. No. 3,481,686), or admixed with other phenolics for the preparation of synthetic detergent-disinfectant or germicidal agents (U.S. Pat. No. 3,824,190).

Addition of hydrogen to furan compounds may proceed by way of a hydrogenation reaction to product partially saturated or saturated compounds and by way of a hydrogenolysis reaction which involves cleavage of the carbon-oxygen bond or bonds and cleavage of carbon-carbon bonds. The prior art is replete with examples of both types of reactions using both catalytic and noncatalytic systems. Consequently it is obvious from the prior art that the hydrogenolysis reaction may be carried out in a facile manner for many of the furans, however, the prior art does not teach the hydrogenolysis of dibenzofuran, in particular, especially for the preparation of orthophenylphenol.

For example, a method for the cleavage of the furans at the carbon-oxygen bond is described in work done by Smith and Fuzek [J. Amer. Chem. Soc., 71, 415 (1949)] using a platinum catalyst in acetic acid solution in the presence of hydrogen. The reaction is carried out in a constant temperature water bath at low pressure. All the furans studied in this work are successfully cleaved using this method with the exception of dibenzofuran. The product of the reaction was dibenzofuran is used as a substrate involves the hydrogenation of both phenyl nuclei to give dicyclohexylene oxide. This is the only furan studied which does not cleave to a major extent.

Another method known in the art is the hydrogenolysis of dibenzofuran to give orthophenylphenol by way of reacting lithium metal with dibenzofuran in refluxing dioxane to form the lithium derivative of orthophenylphenol, followed by water-dioxane hydrolysis to give orthophenylphenol and other side products. This work was carried out by Gilman and Esmay [J. Amer. Chem. Soc., 20, 2947 (1953)]. Since the reaction of this process requires stoichiometric amounts of the alkali metal, the process cannot compete economically with the process of this invention.

The prior art as taught by Landa and co-workers [Sb. Vysoke Skoly Chem.-Technol. Praze, Technol. Paliv, 16, 159–70 (1969)] discloses that $MoS_2$ has been used as a catalyst for the hydrogenolysis of dibenzofuran to give orthophenylphenol. The reaction cited was carried out in a batch reactor charged with about 29 grams (0.17 moles) dibenzofuran and 4 grams MoS$_2$ having a surface area of 31 m$^2$/gram. The reaction was allowed to continue for 30 minutes at 300° C and at a pressure that would be consistent with charging the reactor with 100 atmospheres of hydrogen gas at 17° C. The resulting product consisted of partially saturated and saturated derivatives of dibenzofuran as well as orthophenylphenol, the selectivity to orthophenylphenol product was only 33% at a conversion of 66%. A distinct advantage of the process of this invention over this prior art is the favorable selectivity of this invention to form orthophenylphenol.

The prior art according to Chandler and Sasse [*Aust. J. Chem.*, 16, No. 1, 20 (1963)] teaches the use of Raney nickel for the hydrogenolysis of dibenzofuran by refluxing in methanol in the presence of hydrogen for about 16 hours. No orthophenylphenol is obtained. Instead, a partially saturated product is produced, namely phenylcyclohexanol. The disadvantage of this process, when compared to the process of this invention is the necessity of a dehydrogenation step in order to obtain the desired product of this invention. Thus Chandler and Sasse would require a two step process. The present invention teaches a viable one step process for the production of orthophenylphenol.

Likewise, Papa, Schwenk, and Ginsburg [*J. Org. Chem.*, 16, 253 (1951)] carried out experimental work in which hydrogenolysis of the carbon-oxygen bond in furan compounds was brought about in the presence of nickel-aluminum alloy and aqueous alkali. These compounds yielded approximately equal amounts of two products, one resulting from the hydrogenation of the furan ring, the other a product of the hydrogenolysis of the furan ring. Of the furans tested, only dibenzofuran was substantially unreactive, i.e., only a small amount of phenolic material tentatively identified as orthophenylphenol was obtained. On the other hand, coumarilic acid, unlike dibenzofuran, gave good yields of its hydrogenolysis product β-(orthohydroxyphenyl)-propionic acid. Here again, as described in the work by Chandler and Sasse as well as Smith and Fuzek, little if any of the desired product is being formed in a one step reaction of the type described for the process of this invention.

Other approaches involving classical organic syntheses are described in the prior art, however the methods employed may result in the formation of the mixed isomers, i.e., ortho, para, and metaphenylphenol. This would not be desirable from the standpoint that of the three isomers formed, orthophenylphenol is the most effective as a biocidal agent. The other isomers, i.e., para- and metaphenylphenol, have been demonstrated to be biocidal agents with lesser degrees of effectiveness and, therefore, would only serve as diluents for this application. In addition the para and meta isomers would represent a product loss for the utility of the present invention, since the primary product desired is orthophenylphenol.

Application of Group VIII elements in the form of supported catalysts for the hydrogenolysis of simple furan structures, e.g., 2-methylfuran or 2-vinylfuran, is described in the art by Shuikin, Bel'skii, and Minachev, [*J. General Chem. USSR*, 29, 2932 (1959)]. For example, the hydrogenolysis of 2-methylfuran is carried out in the vapor phase at 275° C in the presence of a platinum on carbon catalyst and hydrogen to give a substantial amount of methylpropyl ketone product. Here again, however, only simple furan compounds were successfully cleaved at the carbon-oxygen bond.

It has now been found that control of conditions is important, i.e., rising temperature favors the hydrogenolysis reaction, while decreasing temperature favors the hydrogenation reaction. Likewise the pressure may serve an important function in the reaction. Most importantly, for the process of this invention, is the ability to select a combination of catalyst and conditions that will selectively cleave the furan ring in dibenzofuran and its derivatives at the carbon to oxygen linkage without substantially hydrogenating the unsaturated portion of the structure or without cleaving the phenyl to phenyl linkage previously designated as the bond between carbons 9$a$ and 9$b$.

It is, therefore, an object of the present invention to overcome the above disadvantages and thus provide an improved and more economical and commercially feasible hydrogenolysis process for the production of orthophenylphenol and its derivatives from dibenzofuran and its derivatives.

Another object of this invention is to provide a catalyst system for a viable one step hydrogenolysis process for the production of orthophenylphenol and its derivatives from dibenzofuran and its derivatives.

Another object of this invention is to provide a reactive, yet stable hydrogenolysis catalyst system that may be operated selectively to produce high yield of the preferred orthophenylphenol product.

These and other objects of the present invention will become apparent to those skilled in the art from the accompanying description and disclosure.

SUMMARY OF THE INVENTION

The process of this invention may be carried out in either the vapor phase or liquid phase, but preferably carried out under conditions in which the dibenzofuran and its derivatives are in the vapor phase. The temperature for this process may be in the range of about 260° C to 500° C, but preferably about 300° C to 500° C, or still more preferably from 350° C to 475° C. At temperatures below about 260° C the undesirable hydrogenation reaction may occur and above about 500° C the catalyst life may be decreased. More particularly the process of this invention may be carried out at a pressure in the range of about 0.1 to 140 atmospheres, wherein the gas hourly space velocity (GHSV) is controlled to operate in the range of about 1 hr$^{-1}$ to 10,000 hr$^{-1}$ or higher, but preferably in the range of about 10 hr$^{-1}$ to 5,000 hr$^{-1}$. The molar ratio of hydrogen to dibenzofuran feed may be in the range of about 0.5:1 to 100:1. The process is carried out in the presence of a catalyst comprised of one or more of the Group VIII elements. Preferably the catalyst contains a minor amount of Group VIII element, that is, in the range of about 0.01 to 49% by weight and is supported on a porous basic support composed essentially of magnesia. However, if consideration is given to the cost of certain Group VIII elements, it is immediately recognized that a more preferable range for certain of the Group VIII elements may be about 0.01 to 5% by weight. The conditions and catalyst for the process of this invention may be selected to advantageously promote selective hydrogenolysis of dibenzofuran to form orthophenylphenol.

DESCRIPTION OF THE PREFERRED EMBODIMENTS

The preferred catalyst for the process of this invention is comprised of minor amounts of one or more Group VIII elements, in the range of about 0.01 to 49% by weight, and more preferably, with cost consideration for certain of the Group VIII elements, in the range of about 0.01 to 5% by weight, and may be on a support which is in the form of powders, granules, spheres, tablets, extrudates, and other forms thereof. It may be prepared for example by impregnating a porous basic support with a compound of a Group VIII element which is subsequently decomposed. Depending on the type of decomposition carried out for the compound, the active may be in one or more possible forms, for example, as an oxide, sulfide, hydride, or the zero valent metal.

Porous basic supports may be used as the catalyst carrier for the process of this invention, such as magnesia, calcia, strontia, baria, magnesium carbonate, calcium carbonate, strontium carbonate, barium carbonate or the like and mixtures thereof, and magnesia is particularly illustrated as suitable in the exemplifications.

These porous basic supports may be obtained from any suitable source that will provide a material having the desired purity. These catalyst carriers should be substantially free from substances or metals that are known or may prove to be poisons for the catalyst of this invention.

The surface area for these catalyst carriers may be in the range of about 1 to 10,000 $m^2$/gram or higher, or preferably about 10 to 2,000 $m^2$/gram.

A catalyst may typically be prepared, using the following method. An impregnation solution comprised of an appropriate amount of soluble Group VIII metal compound dissolved in distilled water, or other suitable solvent, and diluted to the desired volume, preferably in excess of the solution absorptivity of the support. The support is intermingled with said solution and the resulting mixture is stirred for about 5 minutes at ambient conditions followed by slow removal of water by stirring and passing a soft air flow over the preparation to give a free-flowing material. Further drying may be accomplished by mild heating. The still damp preparation is finally dried over a period of about 18 hours at about 120° C in a forced air oven.

The dried preparation may be reduced by any suitable method, for example, reduced in hydrogen gas at about 450° C for about 4 hours or chemically reduced using an aqueous formaldehyde-KOH solution. The latter reduction method may require an additional step of base neutralization, water washing, and drying before the catalyst is used. If desired, the catalyst may be reduced in situ after being charged to the reactor.

According to a preferred feature of the invention, the catalyst is contacted during the reaction with the dibenzofuran, at the same time the catalyst is contacted during the reaction with a gas stream comprised of hydrogen or hydrogen mixed with water vapor or an inert gas such as nitrogen, argon, or helium. The gases and dibenzofuran may be preheated to reaction temperature prior to being introduced into the reactor containing the heated catalyst and said gases and dibenzofuran may be brought into contact with the catalyst by either upward or downward flow through the catalyst bed. The reactor effluent stream containing the orthophenylphenol product may be recycled back through the reactor or may be withdrawn continuously, followed by a product separation and subsequent recycle of the unreacted substrate if desired. The temperature of the reactor may be controlled by conventional means, to maintain the desired operating condition.

After a period of operation when the catalyst may become deactivated by the presence of carbonaceous deposits, the catalyst may be reactivated or regenerated by passing an oxygen containing gas, for example air, air mixed with nitrogen, or air mixed with steam, into contact with the catalyst at an elevated temperature in order to burn the carbonaceous deposits from the catalyst. The method of regenerating the catalyst will depend on whether there is a fixed bed, moving bed, or fluidized bed operation. Regeneration methods and conditions are well known in the art.

Also taught in this invention is that the reaction may be carried out in the liquid phase. For example, in a batch reactor the catalyst may be intermingled with dibenzofuran and hydrogen gas at a temperature in the range of about 350° C to 500° C, but preferably about 400° C to 450° C, and at a pressure of about 70 atm. or broadly from 3 to 200 atm., for a period of about 6 hours. A suitable solvent may be used if desired, a suitable solvent, for example, may be biphenyl, 1-methylnaphthalene, or dibenzofuran itself. Conventional methods of agitation for batch reactors may be used, such as rotating, rocking, or stirring. The reaction product may be separated from the catalyst by way of a built-in filter at the exit of the reactor, leaving said catalyst behind in the reactor for yet another reaction. Although the conditions cited herein for the liquid phase reaction are typical of those used for this type reaction, it is not intended that these conditions should limit the scope in practicing this invention.

The crude orthophenylphenol product produced in either continuous or batch operation or by liquid or vapor phase may be purified, for example, by distillation or caustic-extraction to remove the unreacted dibenzofuran and impurities therefrom.

The following examples illustrate the preparation of orthophenylphenol according to the present invention.

EXAMPLE 1

This example demonstrates that the reaction may be carried out at a reactor pressure of about 8 atmospheres in the presence of a catalyst comprised of palladium on magnesia.

A feed consisting of about 6:1 molar ratio of hydrogen to dibenzofuran is brought in contact with a catalyst comprised of about 0.5% by weight palladium on magnesia, the feed being in the vapor phase at a reaction temperature of about 400° C, and at a total gas hourly space velocity of about 600 $hr^{-1}$. The reactor is operated at a pressure of about 8 atm. The reaction product is dissolved in pyridine and analyzed by gas chromatography. The product contains the following:

|  | Wt. Percent |
|---|---|
| Dibenzofuran | 75 |
| Orthophenylphenol | 23 |
| Others | 2 |

Selectivity to formation of the orthophenylphenol product is 92% at a 25% conversion of the dibenzofuran.

EXAMPLE 2

This example demonstrates that the reaction may be carried out at a space velocity of about 10 hr$^{-1}$ GHSV.

Example 1 is repeated except at a total gas hourly space velocity of about 10 hr$^{-1}$. The product was analyzed by gas chromatography and found to contain about 44 percent by weight dibenzofuran and 40 percent by weight orthophenylphenol.

EXAMPLE 3

This example demonstrates that the reaction may be carried out in the presence of a catalyst comprised of 0.05 percent by weight of a Group VIII metal.

Example 1 is repeated except that the catalyst is comprised of 0.05 percent by weight palladium on magnesia. At 20 percent conversion of the dibenzofuran, the selectivity to orthophenylphenol is 90 percent.

EXAMPLE 4

This example demonstrates that the reaction may be carried out in the presence of a catalyst which has been regenerated.

Example 3 is repeated and after a period of 6 hours, the feeding of dibenzofuran and hydrogen is stopped and the catalyst is regenerated for a period of 6 hours at 450° C using a gas stream containing 2.3% oxygen. The catalyst temperature is then adjusted to 400° C, flow of the regeneration gas stopped and the catalyst reduced in flowing hydrogen for a period of 1 hour.

The reaction conditions of Example 3 are again repeated. After a period of time, the reaction product is analyzed by gas chromatography and found to contain about 80% by weight dibenzofuran and 18% by weight orthophenylphenol.

EXAMPLE 5

This example demonstrates that the reaction may be carried out in the presence of a caalyst comprised of platinum as the Group VIII metal.

Example 1 is repeated except at a reaction temperature of 405° C and a catalyst comprised of about 0.5% by weight platinum on magnesia. After a reaction period of three hours, the product is analyzed by gas chromatography. The analysis reflects a dibenzofuran conversion of 47% with an 31% selectivity to orthophenylphenol.

It should be apparent that the particular embodiments chosen to illustrate the invention are not all inclusive and that many changes and variations could be made therein, some of which for example depend upon the activity of the particular catalyst and upon the nature of the starting material. All such changes, modifications, variations or the like, however, which will be apparent to those skilled in the art after considering this disclosure and which do not depart from the spirit and scope of the invention are deemed to be covered by the subjoined claims.

What is claimed is:

1. Process for the production of orthophenylphenol and substituted ortho-phenylphenols which comprises contacting dibenzofuran or a substituted dibenzofuran of the formula

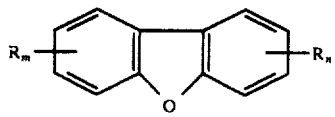

where $m$ is an integer from 1 to 2, $n$ is an integer from 0 to 2, and each R may be selected from the group consisting of lower alkyl, cycloalkyl of 5 to 7 carbon atoms, alkylated cycloalkyl of 6 to 11 carbon atoms, phenyl, benzylphenyl, diphenylyl, alkylated phenyl of 7 to 19 carbon atoms, naphthyl, alkylated naphthyl of 11 to 14 carbon atoms, hydroxyl, carbanol, aldehydo, carboxy and R may also represent the addition of a 4 carbon chain in such a manner as to form a benzoid type fused ring structure in the presence of hydrogen, at a temperature of from 260° C. to 500° C., in the presence of a catalyst consisting essentially of a Group VIII element supported on a porous magnesia support.

2. The process of claim 1 wherein the reaction is carried out in the vapor phase at a temperature of from 300+ C. to 500° C. at a gas hourly space velocity of from 10 hr$^{-1}$ to 5,000 hr$^{-1}$, in the presence of hydrogen at a molar ratio of hydrogen to the dibenzofuran feedstock in the range of 0.5:1 to 100:1.

3. Process as in claim 1, in which the process is conducted in the vapor phase, at a gas hourly space velocity of from 1 hr$^{-1}$ to 10,000 hr$^{-1}$.

4. Process as in claim 1 in which the process is conducted in the vapor phase at a gas hourly space velocity of from 1 hr$^{-1}$ to 10,000 hr$^{-1}$, and the Group VIII element is on a porous basic support composed essentially of magnesia.

5. Process as in claim 2 in which the pressure is from 1 to 100 atmospheres.

6. Process as in claim 2 in which the Group VIII element is palladium on magnesia.

7. Process as in claim 2 in which the Group VIII element is platinum on magnesia.

8. Process as in claim 2 in which the catalyst is regenerated by contacting the catalyst with an oxygen containing gas at a temperature of from 300° C to 700° C, and is then reduced at a temperature of 300° C to 550° C.

9. Process for the preparation of orthophenylphenol which comprises contacting dibenzofuran in the presence of hydrogen at a temperature of from 260° C to 500° C in the presence of a catalyst consisting essentially of a Group VIII element on magnesia.

* * * * *